United States Patent [19]

Spahn et al.

[11] Patent Number: 4,887,715

[45] Date of Patent: Dec. 19, 1989

[54] SURGICAL GAUZE SPONGE MANAGER

[75] Inventors: James G. Spahn, Indianapolis; Steven P. Langley; Michael L. Jacobs, both of Martinsville, all of Ind.

[73] Assignee: Ehob, Inc., Mooresville, Ind.

[21] Appl. No.: 332,769

[22] Filed: Apr. 3, 1989

[51] Int. Cl.4 .................. B65D 85/00; A61B 19/00
[52] U.S. Cl. .................................. 206/370; 206/362; 206/438; 206/526; 229/69; 229/72; 383/39
[58] Field of Search ............... 206/370, 362, 363, 570, 206/572, 209, 210, 438, 440, 526; 229/69, 72; 383/37–39

[56] References Cited

U.S. PATENT DOCUMENTS

| | | | |
|---|---|---|---|
| 847,254 | 3/1907 | Jackson | 383/39 X |
| 3,749,237 | 7/1973 | Dorton | 383/39 X |
| 3,861,521 | 1/1975 | Burtz | 206/370 X |
| 4,190,153 | 2/1980 | Olsen | 206/362 |
| 4,234,086 | 11/1980 | Dorton | 206/362 |
| 4,361,231 | 11/1982 | Patience | 206/362 |
| 4,422,548 | 12/1983 | Cheesman et al. | 206/370 |
| 4,429,789 | 2/1984 | Puckett, Jr. | 206/370 |
| 4,784,267 | 11/1988 | Gessler et al. | 206/438 |

FOREIGN PATENT DOCUMENTS 792087  3/1958  United Kingdom ............... 206/370

Primary Examiner—Bryon P. Gehman
Attorney, Agent, or Firm—Woodard, Emhardt, Naughton, Moriarty & McNett

[57] ABSTRACT

A surgical gauze sponge manager to receive a predetermined number of discarded surgical gauze sponges and to contain the bodily fluids absorbed therein, comprising a finite number of dimensionally controlled pockets to receive an equivalent number of discarded surgical gauze sponges, which pockets are in fluid communication with bodily fluid reservoirs, and which are foldable within an interconnected containment pocket, the pockets being constructed from a semi-transparent material that can be sterilized, and that retains at least semi-transparency when no more than two layers are overlayed, but becomes substantially opaque when at least four layers are overlayed.

6 Claims, 5 Drawing Sheets

SURGICAL GAUZE SPONGE MANAGER

The present invention relates generally to the field of surgical apparatus, and more particularly, to a surgical gauze sponge manager that provides the means by which a precise count of the sponges that have been used during surgeries may be maintained in the sterile surgical field, and that also provides the means by which bodily fluids trapped by discarded sponges may be contained for safe removal and ultimate disposal.

An absolute count of the surgical gauze sponges that have been used during surgeries must be maintained, and the whereabouts of each sponge that enters the sterile surgical field must be accounted for both during and after surgeries. As each surgical layer is closed, for example, the surgical team must absolutely account for the whereabouts of each sponge used to that point. A single missing and unaccounted for sponge means costly delays while a search for the missing sponge is conducted. X-ray machines may have to be brought into the surgery to x-ray the patient for the telltale radiopaque tracer built into each sponge to determine if a missing sponge was inadvertently closed within the patient. Obviously, if that is the case, any closed layers must be reopened until the missing sponge is physically located.

Two to three hundred standard sized 4×4 inch surgical gauze sponges may be used in a typical surgery. Approximately four million packages of ten count 4×4 inch surgical gauze sponges are used in surgeries in the United States each year. Each one of these sponges that enters a sterile surgical field must be absolutely accounted for by a surgical team before a surgery is completed.

Typically, surgical gauze sponges discarded by the surgeon(s) are removed from the sterile surgical field and are randomly collected together somewhere within the surgery room. As each surgical layer is closed, the collection of discarded sponges, wherever they may lie, must be painstakingly separated and counted, one-by-one, until each and every sponge that entered the sterile surgical field to that point is accounted for before the surgical procedure can continue or be finalized.

Removal of discarded surgical gauze sponges from the sterile surgical field not only increases the risk that sponges may be misplaced and remain unaccounted for when the next absolute count is required, but removal also broadens the area of potential dissemination of the bodily fluids that have been absorbed by the sponges during surgery. The rising concern over the health risks inherent in a surgical team's physical contact with bodily fluids that may contain such deadly agents as the AIDS and hepatitis B viruses have led to recent promulgation of Occupational Health and Safety Administration regulations that will require the efficient containment and removal of substantially all bodily fluids released during surgeries. Currently known surgical apparatus and procedures for dealing with discarded surgical gauze sponges do not adequately provide for the containment and certain removal of all such absorbed human fluids for safe removal and disposal, beginning within the sterile surgical field.

The invention disclosed and claimed herein provides a novel surgical apparatus that addresses both the problem of maintaining an accurate count of each surgical gauze sponge discarded by the surgeon(s) at the point they are discarded within the sterile surgical field, and also of containing the bodily fluids absorbed within such sponges during surgeries for safe removal and disposal.

SUMMARY OF THE INVENTION

One embodiment of the invention is a surgical gauze sponge manager to receive a predetermined number of discarded sponges and to contain bodily fluids absorbed thereby, comprising a first set of dimensionally controlled pockets, including a plurality of individual pockets, each sized to receive one standard surgical gauze sponge, that are positioned and interconnected together in a side-by-side relationship with each of the pockets being in fluid communication with a common bottom reservoir for collecting bodily fluids draining from the pockets; a second set of dimensionally controlled pockets in mirror image relationship to the first set of pockets, and extending from an edge area adjacent the openings of the first set of pockets, and including a plurality of individual pockets positioned and interconnected together in a side-by-side relationship with each of the pockets being in fluid communication with a second common bottom reservoir for collecting bodily fluids draining from the pockets; side reservoirs positioned and interconnected in a side-by-side relationship with the outermost pockets of the first and the second sets of pockets to collect bodily fluids overflowing the outermost pockets; a containment pocket extending outwardly from a second edge area adjacent the second common bottom reservoir, the opening of the containment pocket also being adjacent the second edge area, and including an inner chamber sized to fully receive the first and second sets of pockets and the side reservoirs when overlayed one upon the other to form a vertical stack; and connecting means interconnecting the first and second sets of pockets and the containment pocket, including interconnecting the second and the first set of pockets together, and interconnecting the containment pocket and the second set of pockets together.

It is an object of the present invention to provide a surgical gauze sponge manager that provides the means by which an absolute count of discarded surgical gauze sponges can be maintained during surgeries.

It is a further object of the present invention to provide a surgical gauze sponge manager that can be sterilized for use within the sterile surgical field.

It is a further object of the present invention to provide a surgical gauze sponge manager that encloses and contains the bodily fluids that have been absorbed by surgical gauze sponges.

It is a further object of the present invention to provide a surgical gauze sponge manager that accommodates a predetermined number of discarded surgical gauze sponges.

It is a further object of the present invention to provide a surgical gauze sponge manager with a dimensionally controlled pockets into which just one surgical gauze sponge of corresponding dimension will be disposed.

It a further object of the present invention to provide a surgical gauze sponge manager that permits a visual verification of the presence or absence of each surgical gauze sponge that has been contained and enclosed therein.

It is a further object of the present invention to provide a surgical gauze sponge manager that can be prepacked with a finite number of sterile surgical gauze sponges and serve as the sterile means by which surgical gauze sponges are first transported to the sterile surgical field.

It is a further object of the present invention to provide a surgical gauze sponge manager that can be prepacked with a finite number of sterile surgical gauze sponges, weighed, and then weighed again after receiving the same finite number of discarded surgical gauze sponges to determine the weight of bodily fluids absorbed by the sponges during surgery.

It is a further object of the present invention to provide a surgical gauze sponge manager that is readily disposable.

Related objects and advantages of the present invention will be apparent from the following description.

DESCRIPTION OF THE PREFERRED EMBODIMENT

Figure 1:
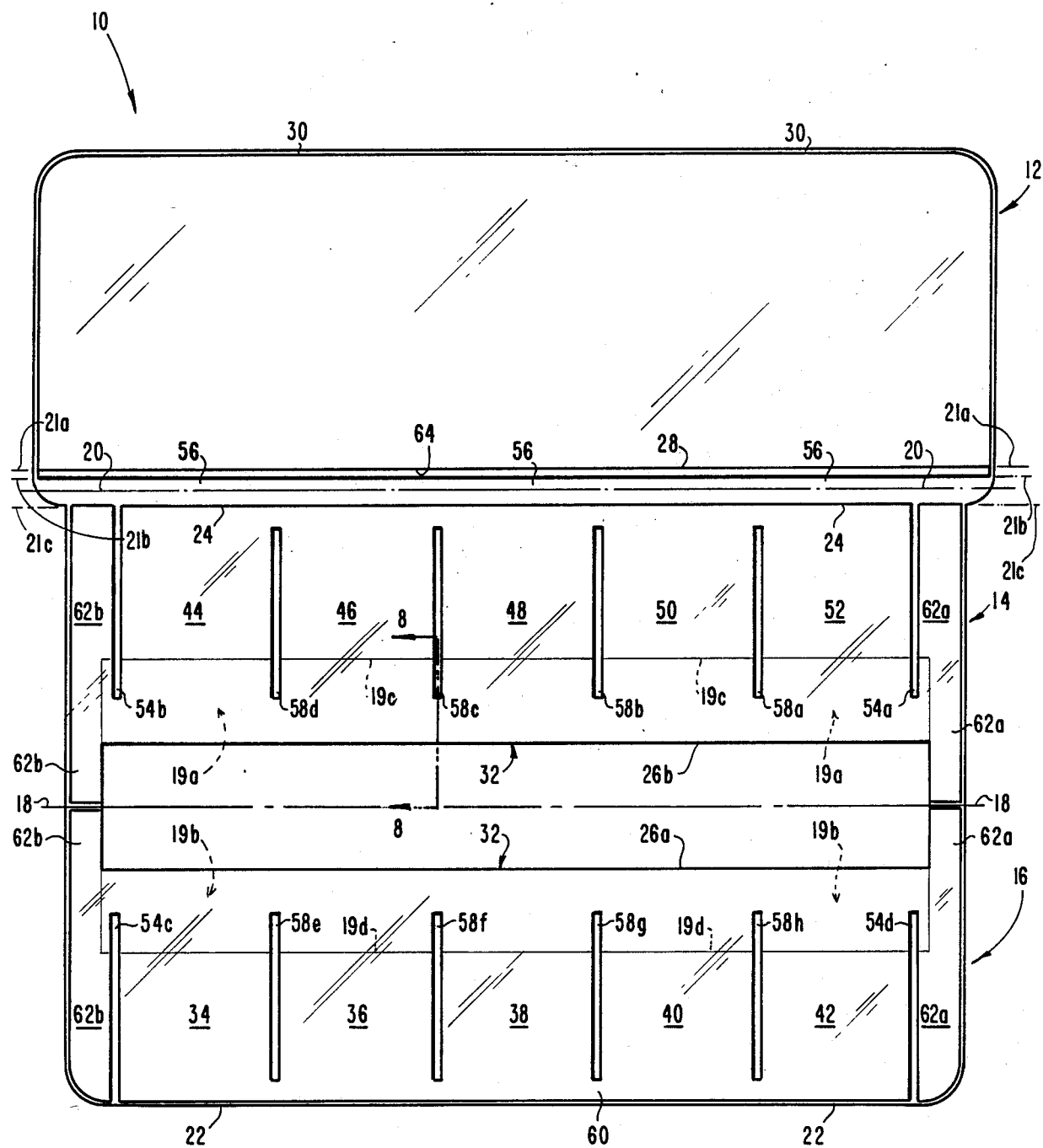
FIG. 1 is a top plan view of a preferred embodiment of the surgical gauze sponge manager 10 of the present invention configured to receive ten 4×4 inch surgical gauze sponges.

For the purposes of promoting an understanding of the principles of the invention, reference will now be made to the embodiment illustrated in the drawings, and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, there is shown in FIG. 1 a top plan view of a preferred embodiment of the surgical gauze sponge manager 10 of the present invention. This preferred embodiment is constructed from two overlayed sheets of 5.5 grade, Federal Drug Administration-approved, semi-transparent, and slightly textured polyvinyl chloride plastic. By comparison, medical blood bags are typically constructed from 6.0 grade, Federal Drug Administration-approved, transparent polyvinyl chloride plastic.

Using conventional polyvinyl chloride plastic heat welding techniques, the two overlayed sheets have been melded together to form a seal approximately 0.06 of an inch wide along the entire periphery of the preferred embodiment of FIG. 1 (i.e, 22 and 30).

Figure 8:
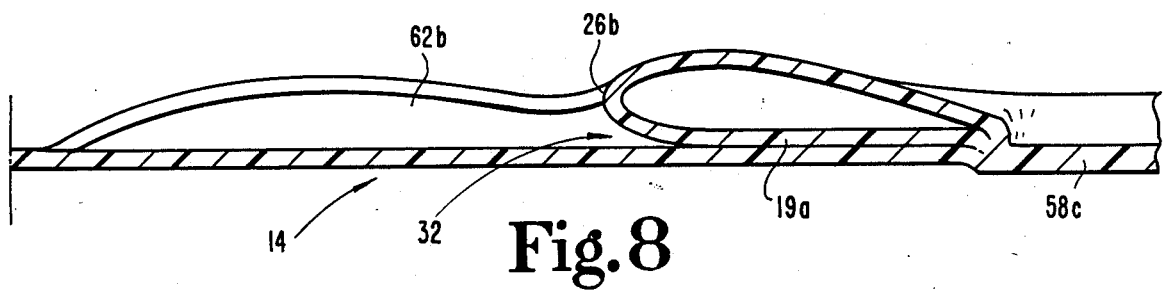
FIG. 8 is an enlarged cross-sectional view of the surgical gauze sponge manager 10 of FIG. 1 taken along line 8—8 in the direction of the arrows.

Referring still to FIG. 1, the topmost sheet of overlayed plastic was cut laterally along line 18—18 across substantially the entire width of the topmost sheet, but stopping well short of the periphery seals described above. At each end of this lateral cut made long line 18—18, the topmost sheet of plastic was also cut longitudinally a short distance on either side of line 18—18 and substantially perpendicular thereto, thus forming two opposing flaps of material lying on either side of line 18—18, each of which was then tucked downwardly toward the bottom most sheet of plastic and away from line 18—18 until disposed between the top and bottom most sheets of plastic as shown in FIG. 1 (19a and 19b). Tuck rolled edges 26a and 26b are thereby defined. FIG. 8 is a cross-sectional view of the above-described flap orientation (19a) and the tuck rolled edge 26b, taken along line 8—8 of FIG. 1, in the direction of the arrows, which includes in cross section bar meld 58c which will be described below.

Referring still to FIG. 1, in the preferred embodiment the topmost plastic sheet was provided with two additional lateral cuts, one each along lines 21a—21a and 21b—21b, with cut abutting but not transgressing the periphery seals, as described above. At each end of these cuts, the topmost plastic sheet was also cut longitudinally between lines 21a—21a and 21b—21b, and substantially perpendicular thereto, thus freeing from the topmost plastic sheet a small ribbon of material, which was removed, thereby defining a containment pocket 12 having an interior chamber 64, which will be described below.

Referring still to FIG. 1, and again employing conventional heat welding techniques, the two overlayed sheets of polyvinyl chloride plastic of the preferred embodiment have been melded together throughout the area 56 lying between line 21b—21b and 21c—21c and the periphery seals described above. Free edge 28 of the topmost sheet of plastic material thus opens to define interior chamber 64 of containment pocket 12, which chamber 64 is defined by edge 28 and the periphery seals about the periphery of containment pocket 12 lying above line 21a—21a in FIG. 1.

Referring still to FIG. 1, the two overlayed sheets of polyvinyl chloride plastic of the preferred embodiment have been melded together along longitudinal bar melds 54a–d and 58a–h, again employing conventional heat welding techniques. Bar melds 54a and 54b extend from edge 24 of area 56 to overlap edge 19c of inwardly tucked flap 19a, as shown in FIG. 1. Similarly, bar melds 54c and 54d extend from the periphery edge 22 to overlap edge 19d of inwardly tucked flap 19b, as shown in FIG. 1. Bar welds 58a–h, on the other hand, each overlap the corresponding edges of tucked flaps 19a and 19b to substantially the same extent as do bar melds 54a–d; however, each bar meld 58a–d stops short of melded area 56 and edge 24 thereof, and each bar meld 58e–h stops short of the periphery edge 22 of FIG. 1. Lastly, bar melds have been made along line 18—18 inwardly from the periphery seals, described above, intersecting line 18—18 to the longitudinal cuts traversing line 18—18 that were described above.

Referring still to FIG. 1, in the preferred embodiment illustrated, bar melds 54a–d and 58a–h define two rows of five opposing pockets, 34 to 42, and 44 to 52, respectively, in mirror image relationship, thus having opposing centralized pocket openings (i.e, 32 identified for opposing pockets 38 and 48 in FIG. 1). The pocket sizes have been dimensionally controlled by selective placement of bar melds 54a–54d and 58a–58h in cooperation with the peripheral dimensions selection, for the surgical gauge sponge manager 10 to correspond inside to one standard surgical gauze sponge in its normal discarded disposition, which is to say, not purposefully compacted or rolled, for example.

In the preferred embodiment illustrated in FIGS. 1–9, pockets 34–52 are dimensionally sized to allow only one standard 4×4 inch surgical gauze sponge to be inserted in a single pocket without stretching or expanding each pocket unduly. However, this is not to imply that it would be impossible for two or more tightly folded gauze sponges to be inserted in any pocket of the preferred embodiment without distortion. It is an object of the present invention to dimensionally control pocket sizes to allow only one standard sized surgical gauze sponge to be inserted therein without a purposeful attempt to stuff two or more such sponges within a single pocket. Furthermore, it is to be understood that although the preferred embodiment as described and illustrated is for use with standard 4×4 inch surgical gauze sponges, the size of pockets 34–52 of the preferred embodiment may be adjusted to accommodate other sizes of surgical gauze sponges and still fall within the scope and intent of the invention.

Referring to FIG. 1 again, the spaces left between bar melds 58a–d and edge 24, and bar melds 58h–e and periphery edge 22 (i.e., 60 at bar meld 58g) define in combination adjoining common bottom reservoirs (60) in fluid communication with pockets 44–52, and 34–42, respectively. Such common bottom reservoirs allow bodily fluids discharged from a discarded surgical gauze sponge placed in any one pocket to be wicked or to flow into the adjoining common bottom reservoir. Similarly, side reservoirs 62a and 62b (see FIG. 8) provided between bar melds 54a–54d and the most proximate periphery seals will trap bodily fluids that laterally overflow from outermost pockets 52, 44, 34 and 42 between respective bar melds 54a–54d and line 18—18 toward the peripheries of surgical gauze sponge manager 10 by actual flow of fluids or by capillary action.

Referring now to FIGS. 2–7, the preferred embodiment 10 of FIG. 1 is illustrated in use. The polyvinyl chloride plastic material selected for the preferred embodiment can be sterilized by gas or cobalt radiation to enable the surgical gauze sponge manager 10 to be used within the sterile surgical field. Sterile surgical gauze sponges, which in the standard 4×4 inch size are commercially packaged in groups of ten, may be brought to the sterile surgical field either independently of the surgical gauze sponge manager 10, or alternatively, the sterilized surgical gauze sponges may be pre-packed within the individual pockets 34–52 of a pre-sterilized surgical gauze sponge manager 10 for transport to the sterile surgical field.

Figure 2:
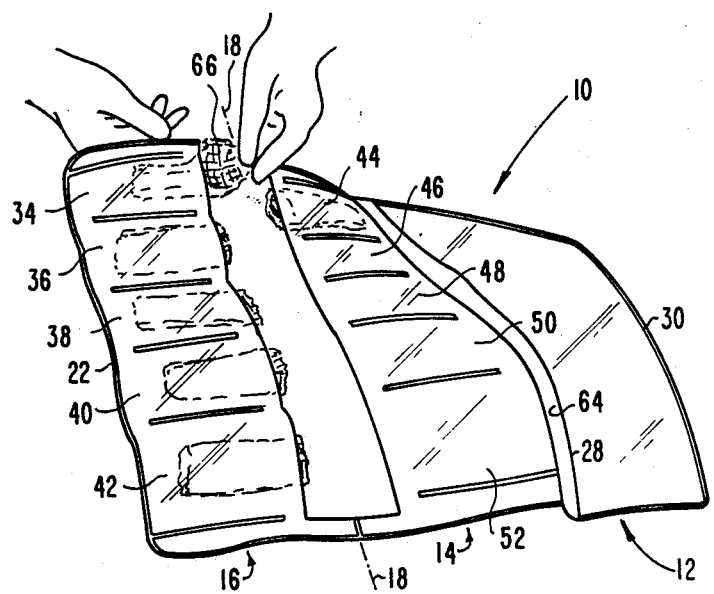
FIG. 2 is a perspective view of the surgical gauze sponge manager of FIG. 1, as it might appear in the sterile surgical field, illustrating a discarded 4×4 inch surgical gauze sponge 66 being placed into one of the ten dimensionally controlled pockets (34) sized to receive just one 4×4 inch surgical gauze sponge.
Figure 3:
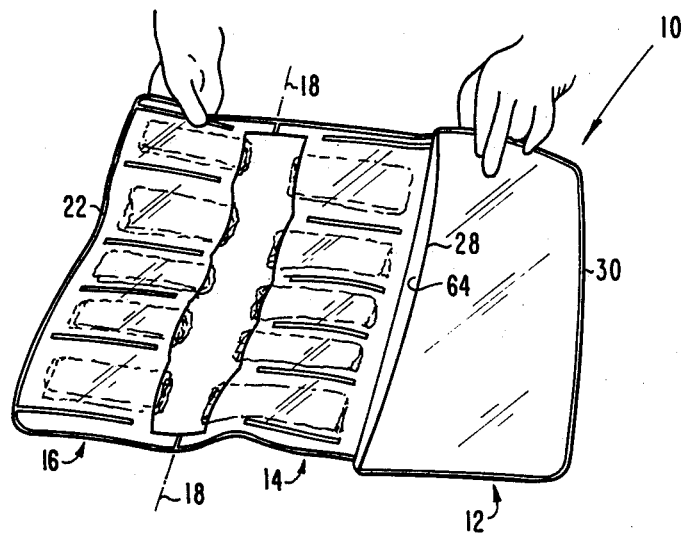
FIG. 3 is a perspective view of the surgical gauze sponge manager 10 of FIG. 2, illustrating ten discarded 4×4 inch surgical gauze sponges contained within ten dimensionally controlled pockets each sized to receive just one 4×4 inch surgical gauze sponge.

Referring now to FIG. 2, typically the surgical gauze sponge manager 10 lies open, as in FIG. 1, on the sterile surgical field. As a 4×4 inch surgical gauze sponge is discarded by the surgeon(s), a member of the surgical team will place each discarded sponge into one of the ten pockets 34–52 of the surgical gauze sponge manager 10. For example, six discarded sponges are shown placed in pockets 34–44 in FIG. 2. The rolled edges 26a and 26b formed by the flap construction (19a and 19b) discussed above present the centralized pocket openings (32) of individual pockets 34–52 in a much better fashion than would a mere cut edge of plastic material. Such rolled edges 26a and 26b allow a discarded surgical gauze sponge (66) to be tucked into each pocket 34–52 with less effort, thus improving the speed and efficiency of surgical gauze sponge disposal. Also, flaps 19a and 19b will tend to trap bodily fluids migrating toward the centralized opening of the individual pockets in the cuffs formed by flaps 19a and 19b.

Figure 4:
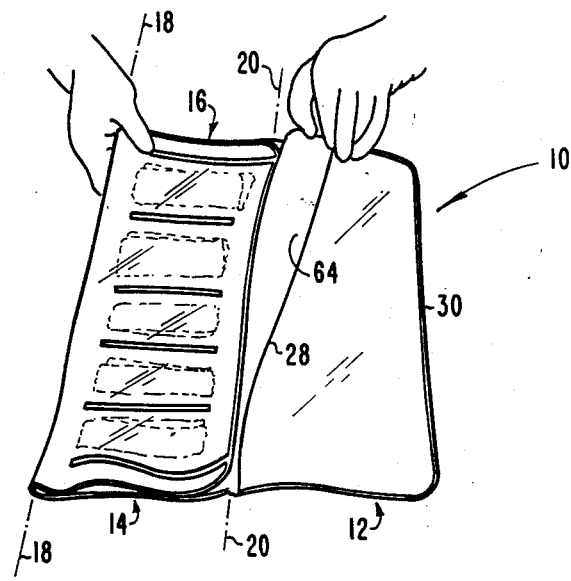
FIG. 4 is a perspective view of the surgical gauze sponge manager of FIG. 3, illustrating the first set of dimensionally controlled pockets 16, overlayed upon the second set of dimensionally controlled pockets 14, first set 16 having been folded from left to right onto the second set 14.
Figure 5:
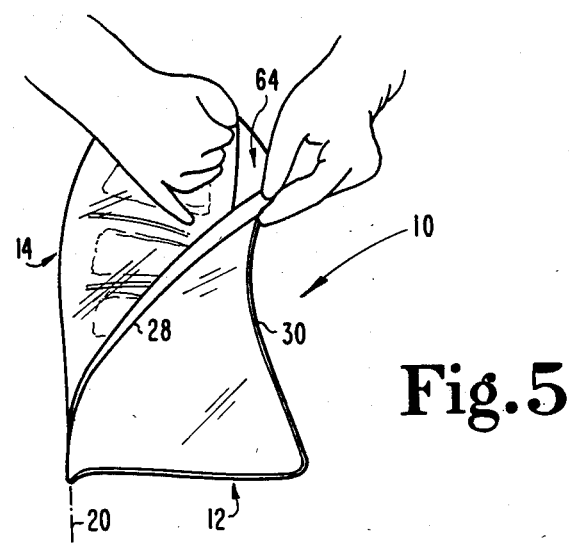
FIG. 5 is a perspective view of the surgical gauze sponge manager of FIG. 4, illustrating the first and second sets of dimensionally controlled pockets 16, 14, overlayed, and being tucked, together, from left to right, into chamber 64 of contingent pocket 12.

When all ten packets 34–52 contain one discarded surgical gauze sponge (FIG. 3), the surgical gauze sponge manager 10 of FIG. 1 is bi-folded as described below for disposal. Referring to FIGS. 1 and 4, pockets 34–42, collectively defining a first set of dimensionally controlled pockets 16, are folded about line 18—18 until the first set of pockets 16 overlay pockets 44–52, collectively defining a second set of dimensionally controlled pockets 14 (FIG. 4), in a vertical stack relationship. Referring now to FIGS. 1, 4, and 5, overlayed first and second sets of pockets 16 and 14 are then folded together about line 20—20 and are tucked within interior chamber 64 of containment pocket 12 (FIGS. 4, 5, and 6).

This bi-fold design allows the first and second sets of pockets 16 and 14 to be fully contained within containment pocket 12 to additionally guarantee entrapment of the bodily fluids absorbed by the discarded surgical gauze sponges 66. As can be readily appreciated, three levels of fluid containment are provided in the illustrated preferred embodiment for the bodily fluids absorbed by discarded surgical gauze sponges: (1) individual pockets 34–52, with their common bottom reservoirs 60, and tuck rolled edges 26a–b at the centralized openings 32; (2) side reservoirs 62a–b at the outermost ends of each set of pockets 16 and 14; and (3) finally containment pocket 12. Containment is so complete that a fair estimate of a patient's fluid loss during surgery can be made by weighing the surgical gauze sponge manager 10 when filled with discarded sponges after surgery to determine and comparing the post-surgery weight with the pre-surgery weight of the surgical gauze sponge manager 10 pre-packed with sterile sponges.

The bi-fold design described for he preferred embodiment also positions the discarded surgical gauze sponges (66) in an overlaying and stacked relationship in two back-to-back rows of five, 180° apart. This allows each discarded sponge to be outwardly visible for a final visual count or accounting (FIGS. 6 and 7). Referring to FIGS. 6 and 7, a member of the surgical team can quickly verify the presence or absence of a surgical gauze sponge in each individual pocket 34–52 by visually inspecting each side of containment pocket 12. In this regard, the tint or transparency of the polyvinyl chloride plastic material chosen must be selected carefully such that when two layers of the plastic material are overlayed the material remains semi-transparent such that an underlying gauze sponge will be visible, but when four layers are overlayed the material becomes substantially opaque such that an underlying gauze sponge will not be visible.

Figure 6:
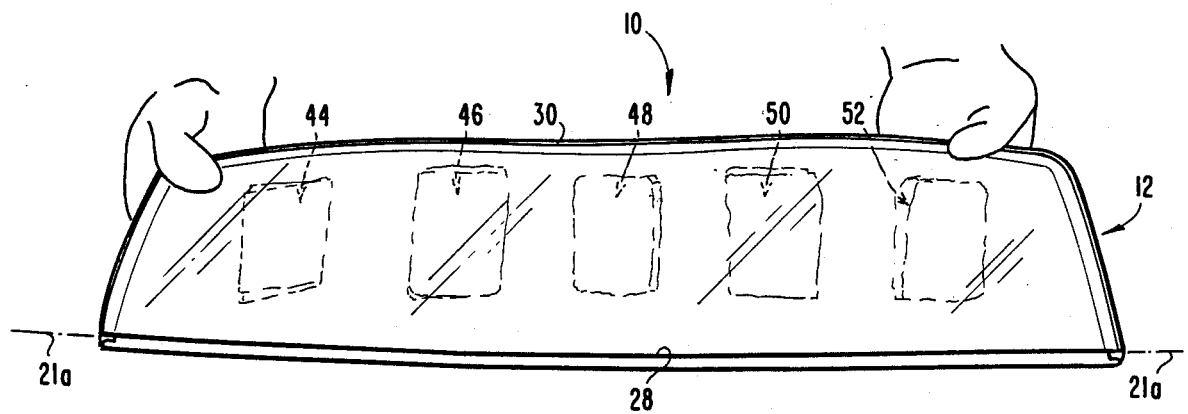
FIG. 6 is a perspective view of the surgical gauze sponge manager 10 of FIG. 5, rotated 90° counterclockwise, illustrating the discarded surgical gauze sponges within the individual pockets 44, 46, 48, 50 and 52 of the second set of dimensionally controlled pockets 14, each sponge being visible through a single layer of the material of containment pocket 12 overlayed upon one layer of the material of each of the individual pockets 44, 46, 48, 50 and 52.
Figure 7:
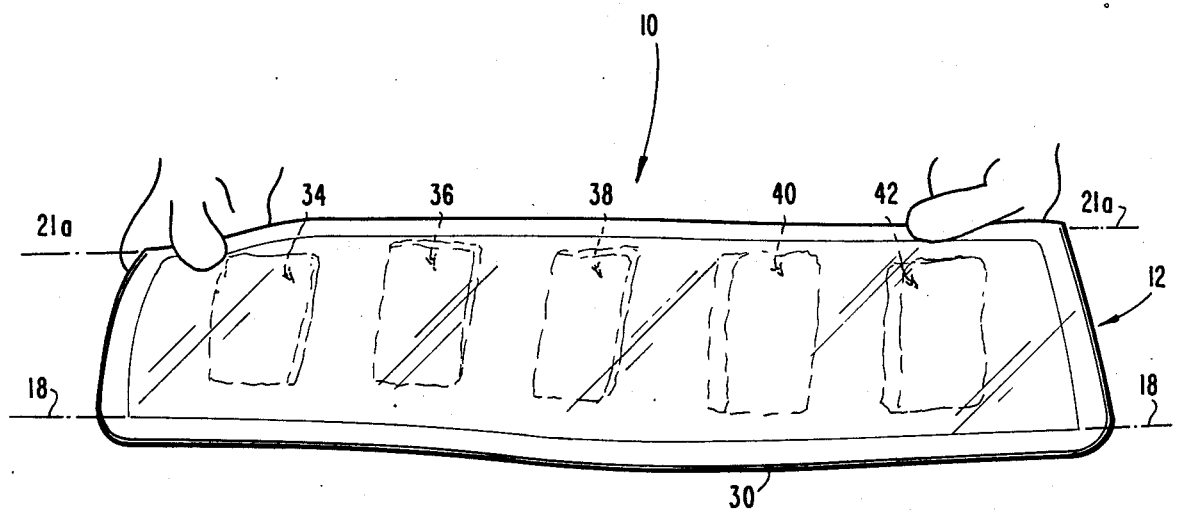
FIG. 7 is a perspective view of the surgical gauze sponge manager of FIG. 6, rotated 180° from back to front, illustrating discarded surgical gauze sponges within the individual pockets 34, 36, 38, 40 and 42 of the first set of dimensionally controlled pockets 16, visible through one layer of the material of the containment pocket 12 overlayed upon one layer of the material of each individual pockets 34, 36, 38, 40, and 42.

Referring to FIGS. 1, 6, and 7, as can be seen from the illustration of FIG. 6, a gauze sponge within pocket 44 must be visible through two sheets of material, one sheet composing one wall of the containment pocket 12 and one sheet composing one wall of individual pocket 44. To prevent a false count, however, if a gauze sponge was missing from pocket 44, the gauze sponge in pocket 34 lying directly below pocket 44 in FIG. 6 (see FIG. 1) must not be visible in FIG. 6, or one might incorrectly perceive that a sponge was present in pocket 44. This false reading possibility is eliminated if the material chosen for the surgical gauze sponge manager 10 becomes opaque when four sheets are overlayed, yet remains at least semi-transparent when only two sheets are overlayed. The proper level of tinting of the polyvinyl chloride plastic material chosen for the preferred embodiment to date to accomplish this limitation can be determined easily by trial and error with material swatches.

To verify the presence or absence of one sponge in each individual pocket 34–42, the surgical gauze sponge manager 10 of FIG. 6 need only be rotated 180°, top to bottom as shown in FIG. 7, to verify the presence or absence of one discarded sponge in each individual pocket 34–42.

When the steps of FIGS. 2–7 have been completed, all within the sterile field, ad the presence of ten surgical gauze sponges in the preferred embodiment have been confirmed accounted for, the surgical gauze sponge manager 10 can be quickly handed off the sterile field for disposal.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical gauze sponge manager to receive a predetermined number of discarded sponges and to contain bodily fluids absorbed thereby, comprising:

a first set of dimensionally controlled pockets, including a plurality of individual pockets each sized to receive one standard surgical gauze sponge that are positioned and interconnected together in a side-by-side relationship with each of said pockets being in fluid communication with a common bottom reservoir for collecting bodily fluids;

a second set of dimensionally controlled pockets in mirror image relationship to said first set of pockets, and extending from an edge area adjacent the openings of said first set of pockets, and including a plurality of individual pockets positioned and interconnected together in a side-by-side relationship with each of said pockets being in fluid communication with a second common bottom reservoir for collecting bodily fluids;

side reservoirs positioned and interconnected in a side-by-side relationship with the outermost pockets of said first and said second sets of pockets to collect bodily fluids overflowing said outermost pockets;

a containment pocket extending outwardly from a second edge area adjacent said second common bottom reservoir, the opening of said containment pocket also being adjacent said second edge area, and including an inner chamber sized to fully receive said first and second sets of pockets and said side reservoirs overlayed one upon the other to form a vertical stack; and connecting means interconnecting said first and second sets of pockets and said containment pocket, including interconnecting said second and said first set of pockets together, and interconnecting said containment pocket and said second set of pockets together.

2. The surgical gauze sponge manager of claim 1 wherein:

said first and second sets of pockets and said containment pocket are constructed from a semi-transparent material that remains semi-transparent when no more than two layers of the material are overlayed yet becomes substantially opaque when at least four layers of the material are overlayed.

3. The surgical gauze sponge manager of claim 2 wherein:

said material can be sterilized for use within the sterile surgical field.

4. The surgical gauze sponge manager of claim 3 wherein:

said material is a Federal Drug Administration-approved plastic sheeting.

5. The surgical gauze sponge manager of claim 4 wherein:

said plastic sheeting is a 5.5 grade polyvinyl chloride.

6. The surgical gauze sponge manager of claim 1 wherein:

each of said individual pockets of said first and second is of dimensionally controlled pockets includes at least one rolled edge at its open end.

* * * * *

UNITED STATES PATENT AND TRADEMARK OFFICE
CERTIFICATE OF CORRECTION

PATENT NO. : 4,887,715

DATED : December 19, 1989

INVENTOR(S) : James G. Spahn, et al.

It is certified that error appears in the above-identified patent and that said Letters Patent is hereby corrected as shown below:

In column 8, line 57, please delete the word "is" and insert in lieu thereof the word --sets--.

Signed and Sealed this

Eighteenth Day of December, 1990

Attest:

HARRY F. MANBECK, JR.

*Attesting Officer*      *Commissioner of Patents and Trademarks*